(12) United States Patent
Boas et al.

(10) Patent No.: US 6,549,284 B1
(45) Date of Patent: Apr. 15, 2003

(54) CALIBRATION METHODS AND SYSTEMS FOR DIFFUSE OPTICAL TOMOGRAPHY AND SPECTROSCOPY

(75) Inventors: David Alan Boas, Newmarket, NH (US); Xuefeng Cheng, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 258 days.

(21) Appl. No.: 09/662,862

(22) Filed: Sep. 15, 2000

Related U.S. Application Data
(60) Provisional application No. 60/154,423, filed on Sep. 17, 2000.

(51) Int. Cl.⁷ .............................................. G01N 21/47
(52) U.S. Cl. ..................................................... 356/446
(58) Field of Search .............................. 356/445, 446, 356/448, 300, 302, 303, 306; 128/633, 664, 665, 634; 250/338.1, 340, 301, 338.01

(56) References Cited

U.S. PATENT DOCUMENTS

| | | |
|---|---|---|
| 5,452,723 A | 9/1995 | Wu et al. |
| 5,517,987 A | 5/1996 | Tsuchiya |
| 5,625,458 A | 4/1997 | Alfano et al. |
| 6,078,833 A | 6/2000 | Hueber |

OTHER PUBLICATIONS

Arridge, "A Finite Element Approach for Modeling Photon Transport in Tissue," *Med. Phys.* 20(2), Pt. 1, Mar./Apr. 1993, pp. 299–309.
Arridge, "Optical Tomography in Medical Imaging," *Inverse Problems*, 15 (1999) R41–R93.
Arridge et al., "Photon–measurement Density Functions. Part 2: Finite–element–method Calculations," *Applied Optics*, 34:34:8026–8037, Dec. 1, 1995.
Farrell et al., "A diffusion Theory Model of Spatially resolved, Steady–state Diffuse Reflectance for the Noninvasive Determination of Tissue Optical Properties in Vivo," pp. 879–888.
Li et al., "Diffraction Tomography for Biochemical Imaging with Diffuse–photon Density Waves," *Optics Letters*, 22:8:573–575, Apr. 15, 1997.

(List continued on next page.)

*Primary Examiner*—Michael P. Stafira
(74) *Attorney, Agent, or Firm*—Fish & Richardson P.C.

(57) ABSTRACT

The invention features a calibration method for diffuse optical measurements that corrects transmittance measurements between a source and a detector for factors unrelated to sample properties. The calibration method is based on the same set of transmittance measurements that are subsequently corrected by the calibration and used in imaging and/or spectroscopy applications. The calibration method involves a forward calculation for each of multiple source-detector pairs based on an approximate model of the sample, and a minimization of an expression that depends on the forward calculations and the transmittance measurements to determine self-consistent coupling coefficients for every source-detector pair. Once the coupling coefficients have been determined, they can be used to correct the transmittance measurements. If desired, an inverse calculation can be performed on the corrected sample measurements to determine spatial variations in the optical properties of the sample. If necessary, the calibration can be repeated and iteratively improved, whereby the optical properties determined by the inverse calculation in an earlier iteration are used to improve the sample model for the forward calculation in a subsequent iteration.

19 Claims, 9 Drawing Sheets

OTHER PUBLICATIONS

O'Leary et al., "Experimental Images of Heterogeneous Turbid Media by Frequency–domain Diffusing–photon Tomography," *Optics Letters,* 20:5:426–428, Mar. 1, 1995.

Patterson et al., "Time Resolved Reflectance and Transmittance for the Non–invasive Measurement of Tissue Optical Properties," *Applied Optics,* 28:12:2331–2336, Jun. 15, 1989.

Siegel, "Design and Evaluation of a Continuous–wave Diffuse Optical Tomography System," *Optics Express,* 4:8:287–298, Apr. 12, 1999.

Wang et al., "MCML—Monte Carlo Modeling of Light Transport in Multi–layered Tissues," *Computer Methods and Programs in Biomedicine,* 47:131–146 (1995).

Yodh et al. "Spectroscopy and Imaging with Diffusing Light," *Physics Today,* pp. 34–40, Mar. 1995.

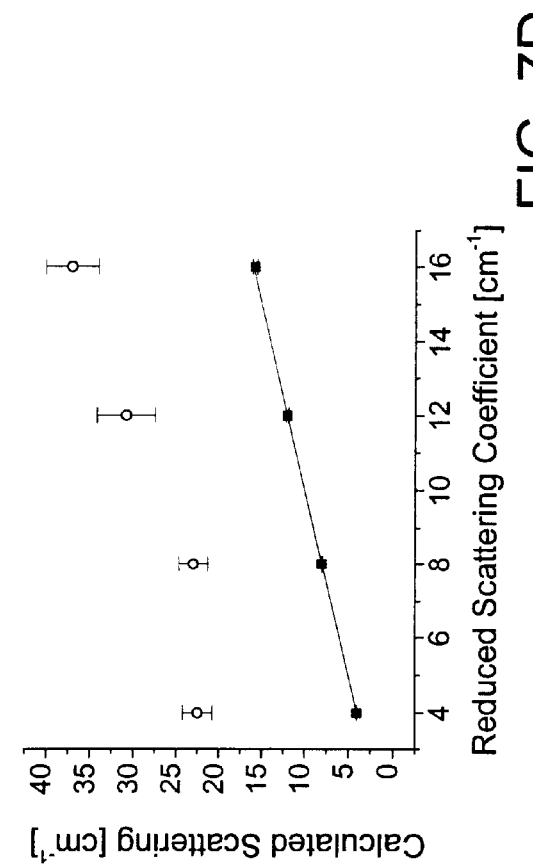
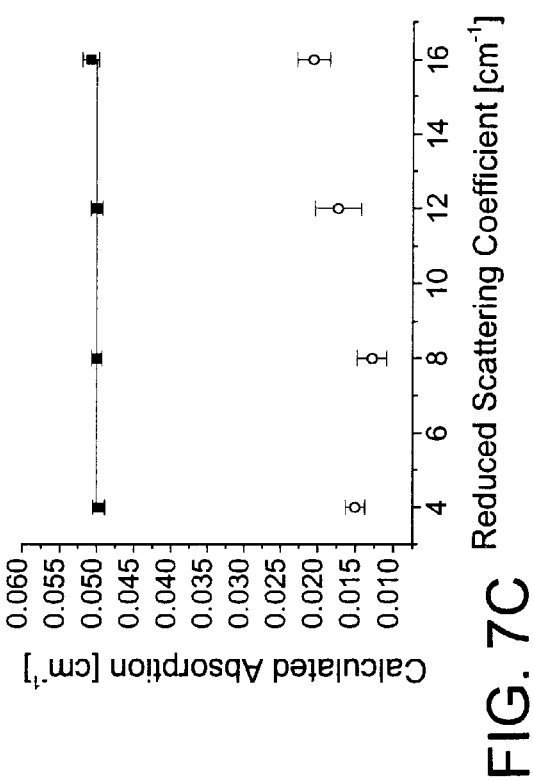
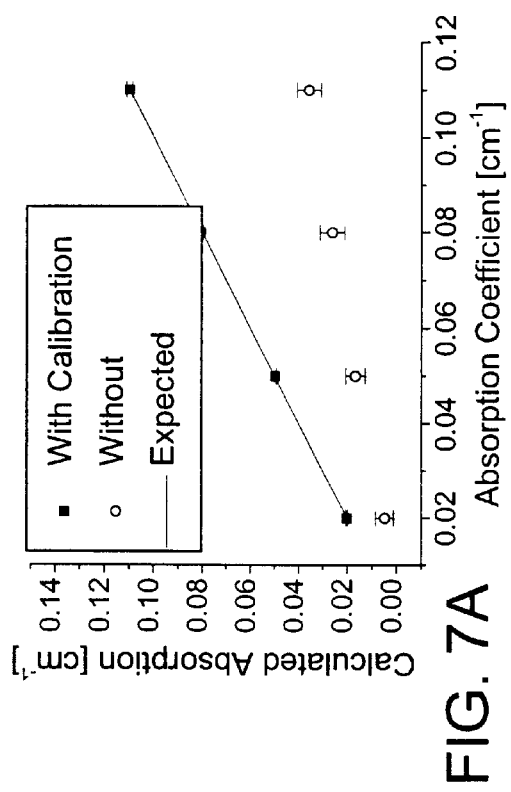
FIG. 7A  FIG. 7B  FIG. 7C  FIG. 7D

Wavelength = 780 nm

Before calibration

After calibration

Wavelength = 830 nm

Before calibration

After calibration

CALIBRATION METHODS AND SYSTEMS FOR DIFFUSE OPTICAL TOMOGRAPHY AND SPECTROSCOPY

CROSS-REFERENCE TO RELATED APPLICATION

This application claims the benefit of U.S. Provisional Application No. 60/154,423, filed on Sep. 17, 2000, which is incorporated herein by reference in its entirety.

FIELD OF THE INVENTION

The invention relates to the calibration of optical techniques for imaging and spectroscopy of, e.g., biological tissue.

BACKGROUND OF THE INVENTION

Recently there has been significant interest in using optical radiation for imaging within highly scattering media, such as biological tissue. Photons travel within the highly scattering media along a distribution of paths, of which very few are straight. Thus, directing light into the highly scattering media and subsequently detecting the diffuse light emitted from the media provides information about local variations in the scattering and absorption coefficients. Such information can identify, for example, an early breast or brain tumor, a small amount of bleeding in the brain, or an early aneurysm. Furthermore, for example, multiple wavelengths can be used to spectroscopically determine local tissue concentrations of oxy-hemoglobin (HbO) and deoxy-hemoglobin (Hb) in tissue, which may be in response to some stimulus, e.g., a drug. For a general description of such applications, see, e.g., A. Yodh and B. Chance in "Spectroscopy and Imaging with Diffusing Light," *Physics Today*, pp. 34–40 (March 1995).

If the spatially varying optical properties of the highly scattering media are known, photon propagation within the media can be calculated numerically. The numerical calculation is simplified when scattering is much larger than absorption, in which case the photon propagation can be approximated as a diffusion process. This condition is typically satisfied in biological tissue in the spectral range of about 700 nm to 900 nm. The numerical calculation gives the distribution of light inside the tissue, and is usually referred to as the "forward calculation." For a sample being imaged, however, the "inverse calculation" needs to be solved, i.e., deducing the sample's optical properties from the diffuse light measurements. Numerical techniques for performing the inversion include singular value decomposition (SVD), simultaneous iterative reconstruction technique (SIRT), K-space diffraction tomography, and using an extended Kaman filter. For a general review of techniques for the forward and inverse calculations, see, e.g., S. R. Arridge in "Optical tomography in medical imaging," *Inverse Problems*, 15:R41–R93 (1999).

In diffuse optical tomography (DOT), multiple sources sequentially direct light into tissue at spatially separated locations, and for each such source, multiple detectors on the tissue measure the diffuse light emitted from the sample at spatially separated locations. For every source-detector pair, one measures the local transmittance of the diffuse light, i.e., the ratio of the diffuse radiance measured by the detector and the incident radiance from the source. The measurements provide the input information for the inverse calculation. However, the measurements can include various uncertainties caused by, for example, fluctuations in the source power, variations in the detector gain, and coupling variations at the source-tissue interface as well as the tissue-detector interface.

To minimize the uncertainties, DOT systems are typically calibrated with initial measurements for a known sample, and the calibration is used to correct subsequent measurements for imaging an unknown sample. Unfortunately, coupling at the source-tissue interface and the tissue-detector interface can vary from measurement to measurement because of, for example, movement or perspiration of the patient, or movement of an optical fiber that forms part of a source or detector. Thus, the results of the inverse calculation can include systematic errors caused by measurement variations that are independent of the tissue optical properties of interest.

The systematic errors can also limit absolute spectroscopic measurements of optical properties at a particular spatial location, e.g., the absolute, rather than relative, values of absorption and scattering.

SUMMARY OF THE INVENTION

The invention features a calibration method for diffuse optical measurements that corrects transmittance measurements between a source land a detector for factors unrelated to sample properties. For imaging applications, the corrected transmittance measurements can be subject to an inverse calculation to determine spatial variations in the optical properties of the sample, i.e., to "image" the sample. For spectroscopic applications, the corrected transmittance measurements can be used to determine absolute values for the optical properties of the sample in a particular spatial region at multiple wavelengths, e.g., to determine the absolute concentrations of oxy-hemoglobin (HbO) and deoxy-hemoglobin (Hb). The calibration method is based on the same set of transmittance measurements that are subsequently corrected by the calibration and used in imaging and/or spectroscopy applications. The accuracy of the subsequent results is thus not subject to uncertainties caused by a delay between calibration and sample measurements.

The calibration method involves a forward calculation for each of multiple source-detector pairs based on an approximate model of the sample, and a minimization of an expression that depends on the forward calculations and the transmittance measurements to determine self-consistent coupling coefficients for every source-detector pair. Once the coupling coefficients have been determined, they can be used to correct the transmittance measurements. If desired, an inverse calculation can be performed on the corrected sample measurements to determine spatial variations in the optical properties of the sample. If necessary, the calibration can be repeated and iteratively improved, whereby the optical properties determined by the inverse calculation in an earlier iteration are used to improve the sample model for the forward calculation in a subsequent iteration.

In general, in one aspect, the invention features a system for making optical measurements. The system includes at least two optical sources which during operation couple optical radiation into a sample at spatially separated locations and at least two optical detectors positioned to receive optical radiation emitted from the sample at spatially separated locations in response to the optical radiation from the sources, and an analyzer.

The signal $g(i,j)$ produced by the $j^{th}$ detector in response to the optical radiation from the $i^{th}$ source can be expressed as $g(i,j)=S^i D^j f(i,j)$, where $f(i,j)$ depends only on the properties of the sample, $S^i$ is a coupling coefficient for the $i^{th}$ source, and $D^j$ is a coupling coefficient the $j^{th}$ detector. During operation, the analyzer calculates the value of the product $S^i D^k$ for at least one of the source-detector pairs based on the signals produced by the detectors and simulated values of $f(i,j)$ corresponding to a model of the optical properties of the sample. The sources, for example, can provide continuous-wave radiation, in which case $g(i,j)$, $f(i,j)$, $S^i$, and $D^j$ are all real-valued. Alternatively, the sources can provide modulated CW radiation, or short temporal pulses of optical radiation (e.g., less than about 1 to 100 ps). In these latter cases, $g(i,j)$, $f(i,j)$, $S^i$, and $D^j$ can be complex, or more generally they can be vectors representing multiple values (e.g., transmittance and temporal delay).

Embodiments of the system can also include any of the following features.

The analyzer can calculate the value of the product $S^i D^j$ for every source-detector pair based on the detector signals and the simulated values of $f(i,j)$. The analyzer can further calculate experimental values of $f(i,j)$ based on the calculated values of $S^i D^j$ and the signals $g(i,j)$ using the expression $g(i,j)=S^i D^j f(i,j)$, and then perform an inverse calculation on the experimental values for $f(i,j)$ to determine spatial variations in at least one optical property of the sample. The optical property or properties can be the absorption coefficient, the reduced scattering coefficient, or both. The analyzer can modify the model of the sample based on the determined spatial variations, and then repeat the calculation of the values of the product $S^i D^j$ for every source-detector pair using the modified model. The initial model can correspond to the sample being homogeneous.

The analyzer can simulate values of $f(i,j)$ according to the expression:

$$f(i,j) \propto \frac{3\mu'_s}{4\pi |r_{ij}|} \exp\left[-(3\mu'_s \mu_a)^{\frac{1}{2}} |r_{ij}|\right]$$

where $|r_{ij}|$ is the distance between the $i^{th}$ source and the $j^{th}$ detector. This expression corresponds to an infinite, homogenous medium.

The analyzer can calculate the value of the product $S^i D^k$ by minimizing the expression:

$$F(S^l D^k) = \sum_{i=1}^{N_s} \sum_{j=1}^{N_d} \left(\frac{L(i,j,k,l)}{S^l D^k} f(i,j) - g(i,j)\right)^2,$$

where $$L(i,j,k,l) = A_s^{ik} A_d^{jl}$$

$$A_s^{ik} = \frac{N_s}{N_d} \sum_{j=1}^{N_d} \frac{g(i,j)}{f(i,j) \cdot \sum_{ii=1}^{N_s} \frac{g(ii,j)}{f(ii,j)} \cdot \frac{f(ii,k)}{g(ii,k)}}$$

$$A_d^{jl} = \frac{N_d}{N_s} \sum_{i=1}^{N_s} \frac{g(i,j)}{f(i,j) \cdot \sum_{jj=1}^{N_d} \frac{g(i,jj)}{f(i,jj)} \cdot \frac{f(l,jj)}{g(l,jj)}}$$

and $N_S$ is the number of sources and $N_D$ is the number of detectors.

Furthermore, when the model corresponds to the sample being homogeneous, the analyzer can calculate at least one of the absorption coefficient $\mu_a$ and the reduced scattering coefficient $\mu'_s$ by minimizing $F(S^l D^k)$ with respect to the product $S^l D^k$ and the at least one of the absorption and scattering coefficients. $F(S^l D^k)$ implicitly depends on $\mu_a$ and $\mu'_s$ through $f(i,j)$. Similarly, the analyzer can calculate both of the absorption and scattering coefficients by minimizing $F(S^l D^k)$ with respect to the product $S^l D^k$ and the absorption and scattering coefficients.

The analyzer can also calculate the product $S^m D^n$ for every source-detector pair by minimizing $F(S^m D^n)$. Alternatively, the analyzer can calculates the product $S^i D^j$ for every remaining source-detector pair according to $$S^i D^j = \frac{L(i,j,k,l)}{S^l D^k}.$$

In another aspect, the invention features a method for calibrating an optical measurement system. The optical measurement system includes at least two optical sources and at least two optical detectors. The sources couple optical radiation into a sample at spatially separated locations and the detectors are positioned to receive optical radiation emitted from the sample at spatially separated locations and generate signals in response to the optical radiation from the sources.

The methods includes the steps of: providing the signals generated by the detectors, wherein the signal $g(i,j)$ generated by the $j^{th}$ detector in response to the optical radiation from the $i^{th}$ source can be expressed as $g(i,j)=S^i D^j f(i,j)$, where $f(i,j)$ depends only on the properties of the sample, $S^i$ is a coupling coefficient for the $i^{th}$ source, and $D^j$ is a coupling coefficient for the $j^{th}$ detector; and calculating the value of the product $S^i D^k$ for at least one of the source-detector pairs based on the signals generated by the detectors and simulated values of $f(i,j)$ corresponding to a model of the optical properties of the sample.

The sources in the optical measurement system, for example, can provide continuous-wave radiation, in which case $g(i,j)$, $f(i,j)$, $S^i$, and $D^j$ are all real-valued. Alternatively, the sources can provide modulated CW radiation, or short temporal pulses of optical radiation (e.g., less than about 1 to 100 ps). In these latter cases, $g(i,j)$, $f(i,j)$, $S^i$, and $D^j$ can be complex, or more generally they can be vectors representing multiple values (e.g., transmittance and temporal delay).

Embodiments of the calibration method can also include any of the following features.

The calibration method can calculate the value of the product $S^i D^j$ for every source-detector pair based on the detector signals and the simulated values of $f(i,j)$. The method can further include calculating experimental values of $f(i,j)$ based on the calculated values of $S^i D^j$ and the signals $g(i,j)$ using the expression $g(i,j)=S^i D^j f(i,j)$, and then performing an inverse calculation on the experimental values for $f(i,j)$ to determine spatial variations in at least one optical property of the sample. The optical property or properties can be the absorption coefficient, the reduced scattering coefficient, or both. Furthermore, the method can include modifying the model of the sample based on the determined spatial variations, and then repeating the calculation of the values of the product $S^i D^j$ for every source-detector pair using the modified model. The initial model can correspond to the sample being homogeneous.

The simulated values of $f(i,j)$ can be calculated according to the expression:

$$f(i, j) \propto \frac{3\mu'_s}{4\pi|r_{ij}|}\exp\left[-(3\mu'_s\mu_a)^{\frac{1}{2}}|r_{ij}|\right]$$

where $|r_{ij}|$ is the distance between the $i^{th}$ source and the $j^{th}$ detector. This expression corresponds to an infinite, homogenous medium.

The method can calculate the value of the product $S^l D^k$ by minimizing the expression:

$$F(S^l D^k) = \sum_{i=1}^{N_s}\sum_{j=1}^{N_d}\left(\frac{L(i, j, k, l)}{S^l D^k}f(i, j) - g(i, j)\right)^2,$$

where $$L(i,j,k,l) = A_s^{ik} A_d^{jl}$$

$$A_s^{ik} = \frac{N_s}{N_d}\sum_{j=1}^{N_d}\frac{g(i, j)}{f(i, j) \cdot \sum_{ii=1}^{N_s}\frac{g(ii, j)}{f(ii, j)} \cdot \frac{f(ii, k)}{g(ii, k)}}$$

$$A_d^{jl} = \frac{N_d}{N_s}\sum_{i=1}^{N_s}\frac{g(i, j)}{f(i, j) \cdot \sum_{jj=1}^{N_d}\frac{g(i, jj)}{f(i, jj)} \cdot \frac{f(l, jj)}{g(l, jj)}}$$

and $N_S$ is the number of sources and $N_D$ is the number of detectors.

Furthermore, when the model corresponds to the sample being homogeneous, the method can include calculating at least one of the absorption coefficient $\mu_a$ and the reduced scattering coefficient $\mu'_s$ by minimizing $F(S^l D^k)$ with respect to the product $S^l D^k$ and the at least one of the absorption and scattering coefficients. $F(S^l D^k)$ implicitly depends on $\mu_a$ and $\mu'_s$ through $f(i,j)$. Similarly, the method can include calculating both of the absorption and scattering coefficients by minimizing $F(S^l D^k)$ with respect to the product $S^l D^k$ and the absorption and scattering coefficients.

The method can also include calculating the product $S^m D^n$ for every source-detector pair by minimizing $F(S^m D^n)$. Alternatively, the method can calculates the product $S^i D^j$ for every remaining source-detector pair according to $$S^i D^j = \frac{L(i, j, k, l)}{S^l D^k}.$$

In another aspect, the invention features a computer-readable medium which causes a processor to perform the steps of any of the embodiments of the calibration method described above.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Embodiments of the invention include many advantages. For example, the new calibration methods eliminate errors caused by using separate data sets to calibrate and image samples. Where the sample is human tissue, such errors can result from patient or fiber movement, or patient perspiration. Furthermore, the calibration method obviates the need to minimize fluctuations in the source outputs and detector gains. Diffuse optical measurement systems employing the new calibration methods can therefore provide more accurate and robust results.

Other features and advantages of the invention will be apparent from the following detailed description, and from the claims.

BRIEF DESCRIPTION OF THE DRAWINGS

FIGS. 7a–7d are graphs of optical coefficients determined in Example 3 based on simulated data.

DETAILED DESCRIPTION

General System

Figure 1:
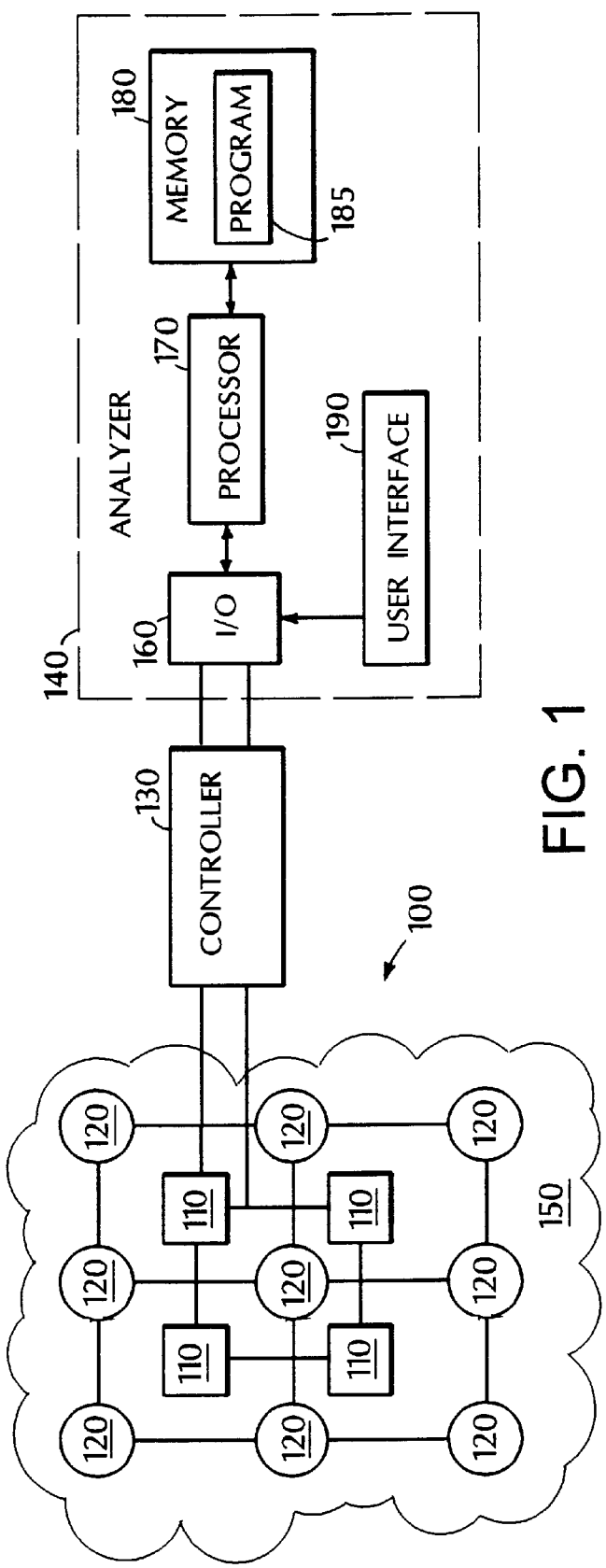
FIG. 1 is a schematic diagram of a diffuse optical tomography (DOT) system.

The invention features a calibration method for a diffuse optical measurement system, e.g., a diffuse optical tomography (DOT) system. A schematic diagram of a DOT system is shown in FIG. 1. The system 100 includes an array of spatially separated light sources 110 and spatially separated detectors 120. During use, the array of sources and detectors is positioned over a sample 150 to be imaged, e.g., a patient's head or breast. A controller 130 connected to light sources 110 sequentially triggers them to couple light into sample 150, which is a highly scattering media that causes the light to become diffuse within the sample. For each sequentially triggered source, each detector 120 measures the light that reaches it through sample 150. Controller 130 is also connected to detectors 120 and selectively channels the signals from the detectors. An analyzer 140 is connected to controller 130 and analyzes the signals measured by detectors 120.

The signal g(i,j) measured by the $j^{th}$ detector in response to light coupled into the sample by the $i^{th}$ source can be expressed as:

$$g(i,j) = S^i D^j f(i,j) \quad (1)$$

where f(i,j) is the transmittance of the sample from the $i^{th}$ source to the $j^{th}$ detector, and $S^i$ and $D^j$ are coupling coefficients for the $i^{th}$ source to the $j^{th}$ detector, respectively. The transmittance f(i,j) depends only on the optical properties, e.g., the spatially varying absorption and scattering coefficients, and can be numerically calculated by a forward calculation if the optical properties are known. Conversely, if the transmittance f(i,j) can be calculated from the measured signals g(i,j), an inverse calculation can be performed on f(i,j) to yield the optical properties of the sample and reveal, e.g., the presence of an object hidden in the sample. The source coupling coefficient $S^i$ includes all of the factors associated with coupling light generated from the $i^{th}$ source into the sample. The detector coupling coefficient $D^j$ includes all of the factors associated with coupling light out of the sample to generate an output signal at the $j^{th}$ detector.

Figure 2:
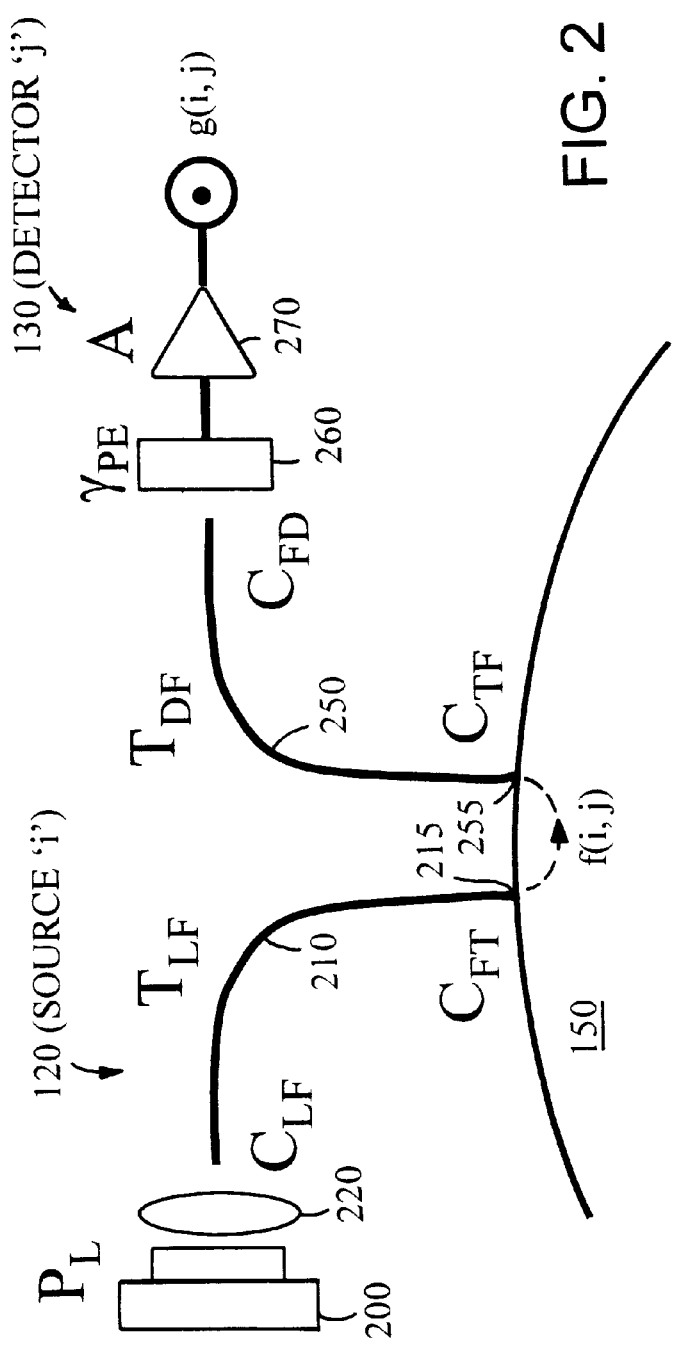
FIG. 2 is a schematic diagram of a source-detector pair for the system of FIG. 1.

For example, in one embodiment shown in FIG. 2, each source 120, e.g., the $i^{th}$ source, includes a diode laser 200 for producing the optical radiation, an optical fiber 210, and a lens 220 for coupling the optical radiation into fiber 210, which includes an end 215 adjacent sample 150 for directing the optical radiation into the sample. Each detector 130, e.g., the $j^{th}$ detector, includes an optical fiber 250 having an end 255 adjacent sample 150 for receiving the optical radiation emitted from sample 150, a photodetector 260 for measuring the intensity of the optical radiation received by fiber 250, and an amplifier 270 for amplifying the output of photodetector 260 to give the measured signal g(i,j). In this embodiment, the source coupling coefficient $S^i$ is the product of the fluence $P_L$ produced by diode laser 200, the coupling coefficient $C_{LF}$ of the lens 220 to the fiber 210, the transmission coefficient $T_{LF}$ of fiber 210, and the coupling coefficient $C_{FT}$ at the interface of fiber 210 and sample 150. Similarly, the detector coupling coefficient $D^j$ is the product of the coupling coefficient $C_{TF}$ at the interface of fiber 250 and sample 150, the transmission coefficient $T_{LF}$ of fiber 260, and the coupling coefficient of the sample fluence produced by the diode laser $P_L$, the coupling coefficient $C_{FD}$ between fiber 260 and photodetector 260, the efficiency $\gamma_{PE}$ of photodetector 260, and the gain A of amplifier 270.

In other embodiments, the light source can include a laser other than a diode laser, e.g., an ultrafast laser, or instead it can include an incoherent source. Also, the sources can include a common light source that selectively couples light into one of multiple fibers that deliver the light to spatially separated locations on the sample. Alternatively, the sources need not include optical fibers at all, for example, the lasers themselves can be positioned adjacent the sample or can include beam delivery optics to direct the light to the sample through free space. Furthermore, the light sources can provide light at multiple wavelengths by including, e.g., multiple diode lasers.

To analyze the measured values g(i,j), a calibration is required to convert the measured values for g(i,j) into the transmittance values f(i,j). According to Equation (1), this requires a calibration for the value of $S^i D^j$ for every source-detector pair. As will be described below, analyzer 140 determines self-consistent values for $S^i D^j$ based on the set of measured values g(i,j) and the results of a numerical calculation for f(i,j) corresponding to an approximate model of the sample. Once the calibration is determined, the same set of measured values g(i,j) can be used to calculate f(i,j) according to Equation (1), from which the analyzer can perform the inverse calculation. Because the same set of measured values are used for the calibration and the inverse calculation, the optical properties determined by the analyzer do not include systematic errors caused by fluctuations in the source and detector coupling coefficients.

In the description that follows, it is assumed that the sources provide CW optical radiation and the detectors measure the intensity of the optical radiation, in which case g(i,j), f(i,j), $S^i$, and $D^j$ are all real-valued. However, the calibration techniques described herein can also be applied to other diffuse optical measurement techniques in which the sources do not provide CW radiation. For example, in some techniques, the amplitude of the optical radiation provided by the source is modulated to create photon density waves in the sample, and the detectors are configured to measure the amplitude and phase of the photon density waves after propagation through the sample. In this case the values for g(i,j), f(i,j), $S^i$, and $D^j$ can be complex. For a general reference on DOT with modulated optical radiation see, e.g., M. A. O'Leary et al., *Phys. Rev. Lett.* 69, 2658 (1992). Furthermore, in other techniques, each source porvides a temporarily coherent light pulse, e.g., a picosecond pulse, and the detectors are time-gated to measure the temporal delay of the diffuse light pulse in addition to its intensity. For a general reference on such time-domain DOT techniques see, e.g., M. S. Patterson et al., *Appl. Opt.* 28, 2331, (1989), and S. R. Arridge in "Optical tomography in medical imaging" ibid.

Calibration Method

Assuming $N_s$ sources and $N_d$ detectors and following Equation (1), the coupling coefficient of the $i^{th}$ source and $j^{th}$ detector can be expressed as:

$$S^i = \frac{1}{N_d} \sum_{j=1}^{N_d} \frac{g(i,j)}{f(i,j) \cdot D^j}, \quad (2)$$

$$D^j = \frac{1}{N_s} \sum_{i=1}^{N_s} \frac{g(i,j)}{f(i,j) \cdot S^i}, \quad (3)$$

$$S^i D^j = \frac{g(i,j)}{f(i,j)}. \quad (4)$$

Equation (2) is the average of all measurements made with source i and Equation (3) is the average of all measurements made with detector j. Substituting Equations (3) and (4) into Equation (2) we obtain a relationship between the source coupling coefficient $S^i$ and the detector coupling coefficient $D^k$, corresponding to the $i^{th}$ source and the $k^{th}$ detector, respectively:

$$S^i = \frac{N_s}{N_d} \sum_{j=1}^{N_d} \frac{g(i,j)}{f(i,j) \cdot \sum_{ii=1}^{N_s} \frac{g(ii,j)}{f(ii,j)} \cdot \frac{f(ii,k)}{g(ii,k)} \cdot D^k} = \frac{A_s^{ik}}{D^k}, \quad (5)$$

and likewise between $D^j$ and $S^l$, corresponding to the source and detector coupling coefficients for the $j^{th}$ detector and the $l^{th}$ source, respectively:

$$D^j = \frac{N_d}{N_s} \sum_{i=1}^{N_s} \frac{g(i,j)}{f(i,j) \cdot \sum_{jj=1}^{N_d} \frac{g(i,jj)}{f(i,jj)} \cdot \frac{f(l,jj)}{g(l,jj)} \cdot S^l} = \frac{A_d^{jl}}{S^l}. \quad (6)$$

Thus, $$S^i D^j = \frac{L(i,j,k,l)}{S^l D^k}, \quad (7)$$

where $$L(i,j,k,l) = A_s^{ik} A_d^{jl} \quad (8).$$

Note that L(i,j,k,l) is a function only of the number of sources and detectors, $N_s$ and $N_d$, the measurements, g(i,j), and the optical properties of the medium as reflected through f(i,j). In other words, L(i,j,k,l) is not dependent on the coupling coefficients.

Combining Equations (2), (3), and (7), the coupling coefficient product $S^l D^k$ must minimize the following expression to be consistent with each other and with the measurements g(i,j):

$$F(S^l D^k) = \sum_{i=1}^{N_s} \sum_{j=1}^{N_d} \left( \frac{L(i,j,k,l)}{S^l D^k} f(i,j) - g(i,j) \right)^2. \quad (9)$$

Assuming that f(i,j) can be calculated from an approximate model, the value for $S^l D^k$ can be calculated by minimizing Equation (9) with respect to $S^l D^k$. The minimization can be repeated for every source-detector pair, or alternatively, once the value for $S^l D^k$ is determined for the l-k source-detector pair, the other coupling coefficient products can be determined from Equation (7). Although the calibration is non-linear, with no unique solution for the individual coupling coefficients $S^i$ and $D^j$, an exact solution exists for the coupling coefficient product of every source-detector pair, which is all that is needed for the calibration. The minimization of Equation (9) can be performed using standard techniques known in the art, see, e.g., W. H. Press et al. in *Numerical Recipes in C: The Art of Scientific Computing* (Cambridge U. Press, New York, 1988).

To perform the minimization in Equation (9), analyzer 140 makes a numerical forward calculation for f(i,j) based on an approximate model of the sample. An initial model can be that the sample is homogenous with a constant absorption coefficient $\mu_a$ and a constant reduced scattering coefficient $\mu'_s$. Once the calibration is performed, an inverse calculation can provide perturbative corrections to the model to show spatial variations in the optical properties of the sample. Numerical techniques for the forward and inverse calculations are known in the art and will be briefly described in the next section. However, for the simple case of an infinite homogeneous sample, the model forward calculation simplifies to the following expression:

$$f(i,j) = \frac{3\mu'_s}{4\pi |r_{ij}|} \exp\left[-(3\mu'_s \mu_a)^{\frac{1}{2}} |r_{ij}|\right], \quad (10)$$

where $|r_{ij}|$ is the distance between the $i^{th}$ source and the $j^{th}$ detector on the sample surface.

If the background optical properties are not known, then an iterative procedure can be used to find $\mu_a$, $\mu'_s$, and the coupling coefficients. The procedure involves estimating $\mu_a$ and $\mu'_s$ to calculate f(i,j), and then minimizing $F(S^l D^k)$ in Equation (9) to find the coupling coefficient $S^l D^k$. The procedure is repeated with different values of $\mu_a$ and $\mu'_s$ in order to minimize $F(\mu_a, \mu'_s, S^l D^k)$ with respect to all three parameters. For spectroscopic applications where constant values of $\mu_a$ and $\mu'_s$ are expected over the spatial extend of the measurement, the technique provides an accurate determination of the absolute values of $\mu_a$ and $\mu'_s$.

Once all of the coupling coefficients $S^i D^j$ are determined based on the initial model calculation, experimental values for f(i,j) are calculated from Equation (1) based on the determined coupling coefficients and the measurements g(i,j). The analyzer then performs an inverse calculation on the experimental values for f(i,j) to determine perturbations to the homogeneous model for the sample. If necessary, the calibration can be repeated for an improved model of the sample based on the results of the inverse calculation. In turn, the inverse calculation can be repeated for experimental values f(i,j) calculated from Equation (1) using the revised calibration. This iterative process can be repeated until the results for the spatially varying optical properties of the sample begin to converge.

Figure 3:
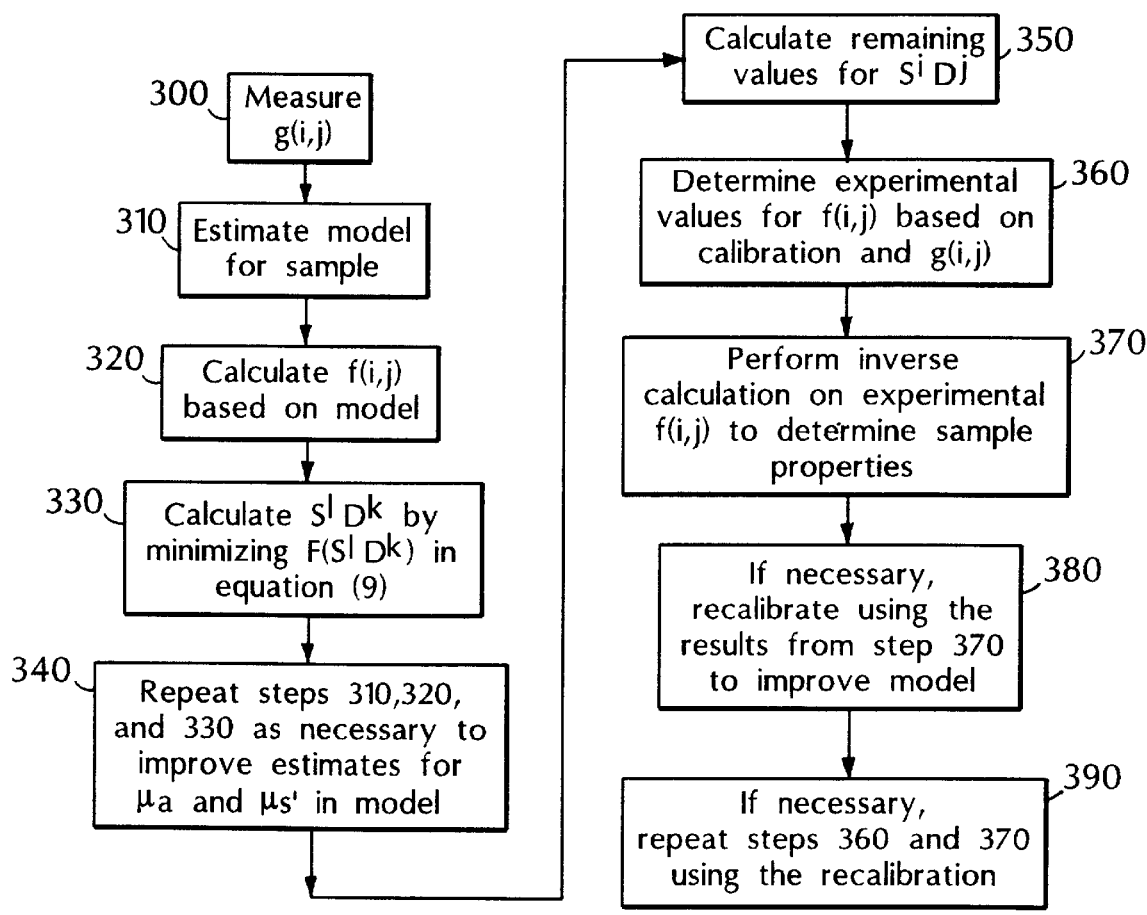
FIG. 3 is a flow chart summarizing the steps of one embodiment of the calibration method described herein.

The steps performed by the analyzer to carry out the calibration and analysis of measurements g(i,j) for imaging applications are summarized by the flow chart in FIG. 3.

In step 300, the analyzer receives measured signals g(i,j) from the detectors.

In step 310, an initial model for the sample is input into the analyzer, for example, the initial model may treat the sample as being homogeneous. In this case, values for $\mu_a$ and $\mu'_s$ are estimated if they are otherwise unknown.

In step 320, the analyzer calculates values for f(i,j) based on the sample model and a forward calculation. For example, if the sample is modeled to be homogeneous and infinite, Equation (10) can be used.

In step 330, the coupling coefficient $S^l D^k$ is determined by minimizing $F(S^l D^k)$ with respect to $S^l D^k$ in Equation (9), the other parameters in Equation (9) being specified by the measurements for g(i,j) and the values for f(i,j) from the model forward calculation in step 320.

In step 340, steps 310–330 are repeated as necessary with additional estimates for $\mu_a$ and $\mu'_s$, until values are found for $S^l D^k$, $\mu_a$, and $\mu'_s$ that optimally minimize $F(S^l D^k)$.

In step 350, the values for all of the remaining coupling coefficients $S^i D^j$ are determined by either: 1) calculating $S^i D^j$ using Equation (7) and the value for $S^l D^k$ determined in step 340; or 2) replacing the argument $S^l D^k$ for F in Equation (9) with the coupling coefficients $S^i D^j$ corresponding to each of the remaining source-detector and determining the value $S^i D^j$ that minimizes F.

In step 360, the calibration coefficients $S^i D^j$ determined in steps 340 and 350, and the measurements g(i,j) from step 300 are used to calculate experimental values for f(i,j) based on Equation (1).

In step 370, an inverse calculation is performed on the experimental values for f(i,j) calculated in step 360 to determine spatial variations in the optical properties of the sample, e.g., an object hidden with a highly scattering sample.

In step 380, if necessary, the model for the sample estimated in step 310 is revised based on the results from step 370, then steps 320, 330, and 350 are repeated, one time, to recalculate the calibration coefficients $S^i D^j$ based on the revised sample model.

In step 390, if necessary, steps 360–370 are repeated, one time, using the recalculated calibration coefficients from step 380 to improve the determination of the spatial variations in the optical properties of the sample. Steps 380–390 can be iteratively repeated as necessary until the spatially varying optical properties determined in step 390 converge to within a desired accuracy.

For spectroscopic applications in which the optical properties of the sample are expected to be homogeneous, the method can be terminated at step 340 because the calibration technique provides direct determination of the absolute values of $\mu_a$ and $\mu'_s$.

Also, in other embodiments, the summations in the Equations above need not be over every source and detector in the experimental apparatus. For example, source-detector measurements between any two sources and any two detectors are sufficient to determine all of the source-detector coupling coefficient products corresponding to that set of sources and detectors. This example would be equivalent to setting $N_s=2$ and $N_d=2$ in the above Equations. Once some of the coupling coefficient products are determined based on a subset of all possible source-detector measurements, the remaining coupling coefficient products can be determined with relatively fewer additional measurements.

Forward and Inverse Calculations

Techniques for the forward and inverse calculations of light propagation within the sample are known in the art. See, e.g., S. R. Arridge in "Optical tomography in medical imaging" ibid. An exemplary formulation of the calculation is described below.

The absorption coefficient $\mu_a$ and diffusion coefficients D, where $D=\upsilon/[3(\mu_a+\mu'_s)]$, are expanded into a spatially independent background term $\mu_a^\circ$ and $D_o$, repsectively, and a perturbative spatially dependent terms $\delta\mu_a(r)$ and $\delta D(r)$, respectively. These terms are then incorporated into the diffusion equation, whose formal solution can be expressed as an integral equation by use of the appropriate Green function corresponding to the sample's boundary conditions.

In the present case, the light energy density is expanded in a perturbative series, i.e., $U(r)=U_0(r)+U_1(r)+\ldots$, and solved to first order. The first-order perturbative solution to the heterogeneous equation, in the limit in which $U_1 \ll U_0$, is given by:

$$U_0(r_s, r_d) = M\, exp(ik_0|r_s-r_d|)/(4\pi D_0|r_s-r_d|) \tag{11}$$

$$U_1(r_s, r_d) = \int_V \left[-\delta\mu_a(r)\upsilon D_0^{-1} U_0(r_s, r)G(r, r_d) + \frac{\delta D(r)}{D_0}\nabla U_0(r_s, r)\cdot \nabla G(r, r_d)\right]d^3r \tag{12}$$

where M is the amplitude of the source located at $r_s$, $G(r,r_d)$ is the Green function solution of the homogeneous equation at detector position $r_d$, $\upsilon$ is the speed of light in the medium, and $k_0=[(-\upsilon\mu_a^\circ+i\omega)/D_o]^{1/2}$ is the photon density wave number, where $\omega$ is the source modulation angular frequency. If an infinite medium is assumed, the Green function is $G(r,r_d)=\exp(ik_0|r-r_d|)/(4\pi|r-r_d|)$. The integral in Equation (12) is over the entire sample volume. In the embodiment described above, the source is a CW source without any modulation. Thus, $\omega$ goes to zero and $k_0$ is purely imaginary, so that both $U_0(r)$ and $U_1(r)$ are real-valued. The first term in the integral of Equation (12) corresponds to absorbing inhomogeneities, whereas the second term corresponds to scattering inhomogeneities. Where it is known that one or other type of inhomogeneity dominates, the non-dominant term can be dropped from Equation (12).

Based on Equations (11) and (12), the forward calculation corresponds to:

$$f(i, j) = \frac{U_0(r_s^{(i)}, r_d^{(j)}) + U_1(r_s^{(i)}, r_d^{(j)})}{M}. \tag{13}$$

In other embodiments, it is also possible to expand the perturbation series beyond the first term.

For the image reconstruction, i.e., the inverse calculation, the integral in Equation (12) is digitized into a sum over voxels (i.e., volume elements), and equated to a series of the values for $U_1$ $(r_s^{(i)}, r_d^{(j)})$, which is extracted from the measurements g(i,j) and the calibration. This yields a set of coupled linear equations that relates to the values of and $\delta\mu_a$ and $\delta D$ in each voxel within the sample, which correspond to spatial variations in $\mu_a$ and $\mu_s$. Many numerical methods are available for solving this system of equations including, for example, the algebraic technique Simultaneous Iterative Reconstruction Technique (SIRT) and single value decomposition (SVD). For a reference on SIRT, see, e.g., A. C. Kak and M. Slaney in *Principles of Computerized Tomographic Imaging*, (IEEE, New York, 1988), Chap. 6, p. 211. For a reference on SVD, see, e.g., W. H. Press et al., ibid. at Chap. 2, p. 52.

Software Implementation

The calibration method can be implemented in hardware or software, or a combination of both. The method can be implemented in computer programs using standard programming techniques following the method and figures described herein. Program code is applied to input data to perform the functions described herein and generate output information. The output information is applied to one or more output devices such as a display monitor.

Each program is preferably implemented in a high level procedural or object oriented programming language to communicate with a computer system. However, the programs can be implemented in assembly or machine language, if desired. In any case, the language can be a compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The calibration method can also be implemented as a computer-readable storage medium, configured with a computer program, where the storage medium so configured causes a computer to operate in a specific and predefined manner to perform the functions described herein.

For example, referring again to FIG. 1, analyzer 140 includes a processor 170, and input/output control card 160, a user interface 190 such as a keyboard and monitor, and a memory 180. The memory stores a program 185 specifying the steps of the calibration method. When executed, the program causes the processor to carry out the steps of the calibration method.

EXAMPLES

Additional aspects, features, and advantages of the invention will now be exemplified in the following non-limiting examples.

1. Diffuse Optical Tomography Apparatus

Figure 4:
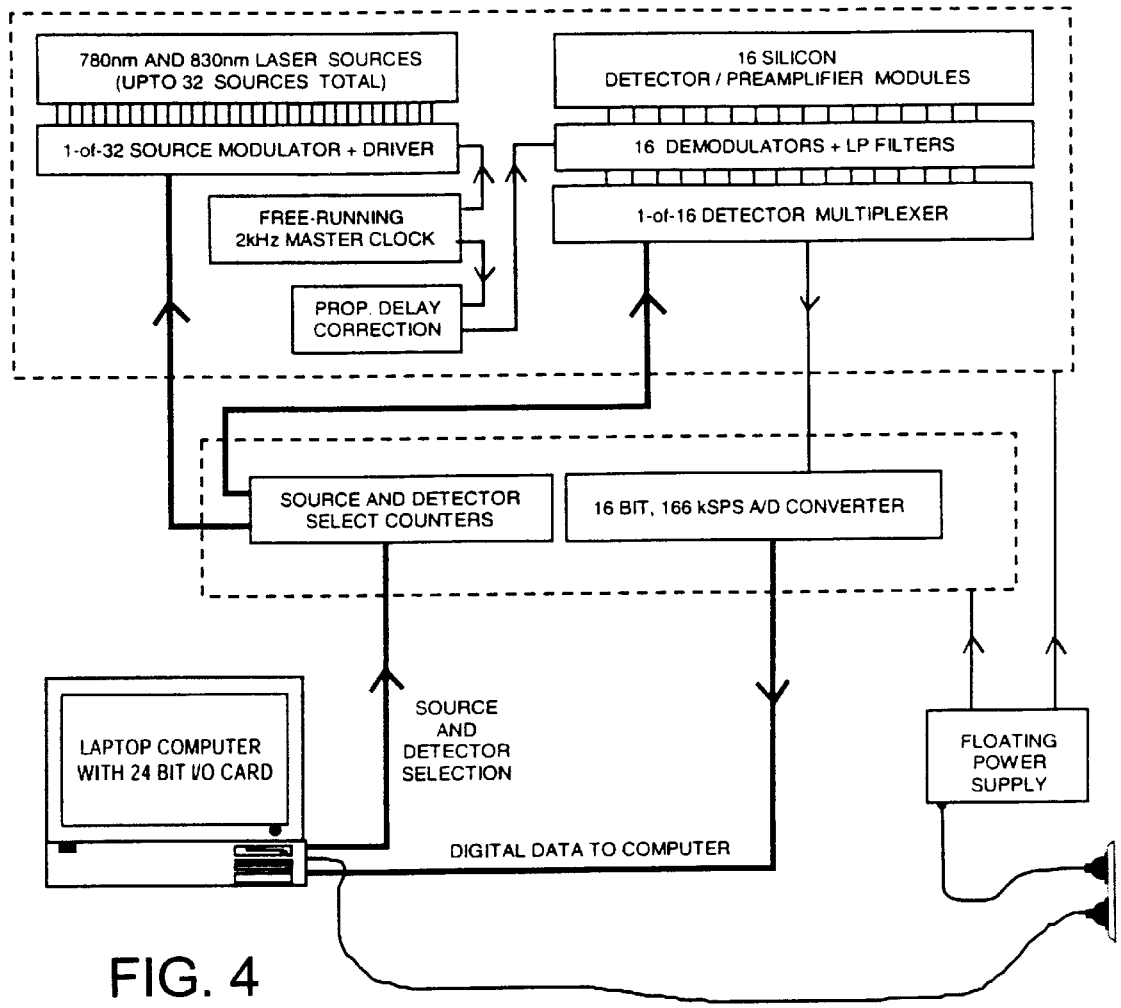
FIG. 4 is a schematic diagram of electronic hardware for the DOT system of Example 1.

A continuous-wave diffuse optical tomography system was built. A schematic of the electronic hardware for the system is shown in FIG. 4.

The optical sources were standard low power diodes, although more powerful light-emitting diodes can also be used. The detector array was a monolithic photodiode/preamplifier IC housed in a clear 8-pin DIP package (OPT209 from Burr-Brown, Tucson, Ariz.). Alternative embodiments for the detectors can range from, e.g., multi-anode PMTs to discrete commercial-grade photodiodes with external preamplifiers.

Optical cross talk was minimized by concealing each detector package in opaque heat shrink tubing and providing sufficient separation to further attenuate any stray reflections within the metal housing. Each detector fiber was sheathed in opaque tubing as well, which also served to protect the fragile cladding of the polymethyl methacrylate (PMMA) fibers from abrasion. Electrical cross talk occurring at the front end was not significant since the only high impedance node in the preamp was physically removed from the DIP package and the modulation frequency was in the kilohertz range. Ground loops were minimized by using an electrically isolated power supply, a battery-powered portable laptop computer, and a single-point earth connection to safety ground. Cross talk through power lines was minimized with on-board regulation and the use of separate power supply decoupling filters at each op-amp. Feedthru among multiple channels within the analog multiplexer was minimized by switching only demodulated (baseband) signals and by reducing the DC currents through the switches by placing a buffer directly at the multiplexer output.

To meet a dynamic range objective of 80 dB objective the system included a 133 kilosample-per-second, 16-bit A/D converter (Analog Devices AD7884). The high sample rate allowed rapid scanning through the 16 demodulated outputs during a high data rate measurements, while still permitting oversampling and subsequent averaging in the digital-domain during slower measurements. The performance goals for the system are shown in Table 1.

TABLE 1

| PARAMETER | GOAL |
| --- | --- |
| DYNAMIC RANGE | 10,000:1 (80 dB) |
| NONLINEARITY | <1% over the 80 dB dynamic range |
| SETTLING TIME | <300 ms to 0.1% |
| CROSSTALK | <0.01% |
| DIGITAL RESOLUTION | 16 bits |
| SOURCE CHANNELS | 9 at 780 nm and 9 at 830 nm |
| SOURCE OPTICAL POWER | ~5 mW |
| DETECTORS | 16 Si photodiode/preamplifiers (OPT209) |
| MODULATION TECHNIQUE | Single-phase squarewave AM with coherent detection |
| POSTDETECTION BANDWIDTH | 10 to 20 Hz |
| STRAY LIGHT REJECTION | <1% error under normal illumination levels |
| PACKAGING ISSUES | Must be portable, compact, and extremely rugged |
| POWER REQUIREMENTS | 120 VAC +/− 10%, 50–60 Hz |
| PATIENT SAFETY | Leakage current <1 $\mu$A, case-to-gnd impedance <1$\Omega$ |

Synchronous detection was used to detect picowatts of source signal under an ambient optical background in the microwatt range (as seen by the detector). In particular, the laser diodes sources were intensity-modulated with a 50% duty cycle by modulating the bias current at 2 kHz. Each photodetector preamp output was high-pass filtered to remove ambient low frequency signals and then fed into a double-balanced mixer. The mixer, which is gated by the same modulator that controls the laser diode source intensity, synchronously rectifies the weak modulated source signal to produce a DC voltage at the mixer output. All other spurious modulated optical signals (including those produced by line-powered lamps, computer terminals, multiplexed LED displays, etc.) exit the mixer as frequency-shifted AC signals. A subsequent low-pass filter strongly attenuates the AC signals, leaving only the DC voltage, which is proportional to the magnitude of the detected source energy. The post-detection time constant was set to 40 ms and the dwell time was set to about 200 ms to provide sufficient settling for each detector channel. A computer was used to select the source and detection channels.

Table 2 below lists performance results for the system.

The system noise floor was obtained by calculating the standard deviation of a number of readings taken at the lowest resolvable source intensity. The noise equivalent power was then calculated for an SNR of unity, using the power-per-unit-flux value obtained from the linearity measurement.

Dynamic range and linearity are related: the dynamic range can only be defined with reference to a specified linearity limit. The incident beam from an optical source was sampled with a "monitor" fiber that led to a calibrated power meter. The linearity was then measured by comparing this value to the system reading over a wide range of flux levels. The flux was varied using neutral density filters. A diffuser was used to reduce the spatial coherence of the source, which prevented modal noise in the fibers from interfering with the measurement.

TABLE 2

| PARAMETER | MEASURED VALUE |
| --- | --- |
| NOISE EQUIVALENT | <40 pW RMS (measured with 32 samples per dwell |
| DYNAMIC RANGE | ~45,000; 1 (92 dB) @ 0.75% nonlinearity<br>~25,000; 1 (88 dB) @ 0.05% nonlinearity |
| LONG-TERM STABILITY | +/−1% if reading in 30 minutes (half-scale output) |
| INTERCHANNEL CROSSTALK | <1:20,000 (−86 dB) |
| STRAY LIGHT REJECTION | ~DN signal change from darkness to normal ambient using cool-white fluorescent and incandescent lamps |
| TEMPORAL RESPONSE | ~20 Hz |
| POWER DELIVERED TO TISSUE | 2 mW @ 780 nm, 8 mW @ 830 nm |

Long-term stability was measured by noting the total drift between initial and final readings for a fixed probe geometry on a static sample. Interchannel cross talk was measured as a single detector channel was alternatively driven between the noise floor and full-scale output using the diffuser/ND filter technique described earlier. The largest level change among the other fifteen channels was recorded. Stray light rejection was measured by operating the system with a static sample in a dark room and then turning on both the fluorescent lights and a computer display located about a meter away. The largest change among the sixteen detector channels was recorded. The detected power in the visible band was ~1.5 uW.

The power delivery was measured at the end of ~1 meter of 1 mm diameter polymethly methacrylate fiber using a calibrated power meter. No index-matching with the detector was attempted. This may underestimate the actual power by ~4% for in-vivo measurements due to index-matching from perspiration trapped at the fiber/skin interface.

2. Experimental Calibration Results with on Bath of Intralipid and India Ink

Figure 5:
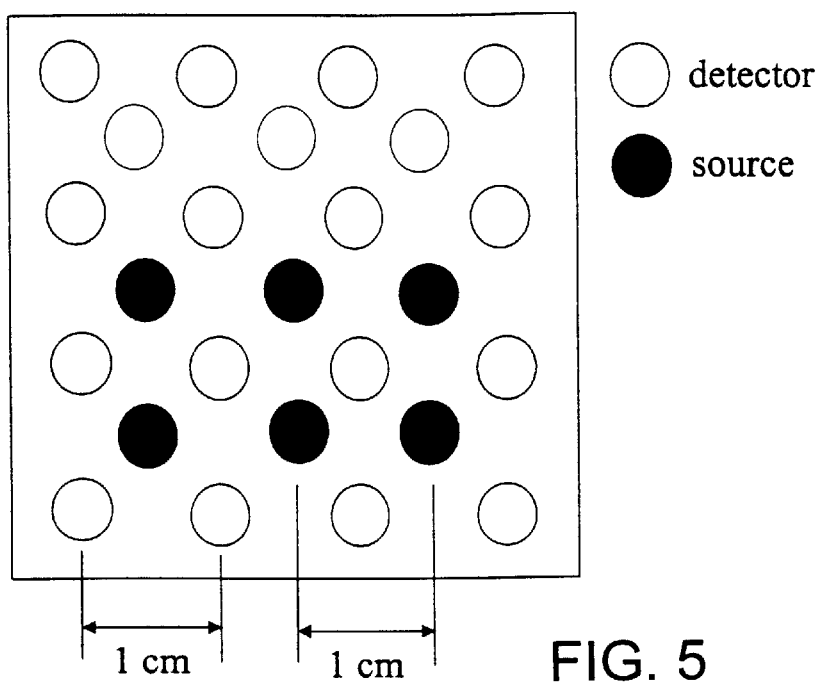
FIG. 5 is a schematic diagram of the optical arrangement of the sources and detectors of Example 2.

Experimental measurements were performed on a bath of highly scattering sample of varying concentrations of Intralipid and India ink using the system described in Example 1. The bath was deep enough to be considered "semi-infinite." The nine sources and sixteen detectors used in the measurement are shown in FIG. 5. The distance between neighboring detectors and neighboring sources is 1 cm. The experimental set-up was fixed and therefore the coupling coefficients of all channels were nearly constant in time although they were different from each other and unknown.

Figure 6A:
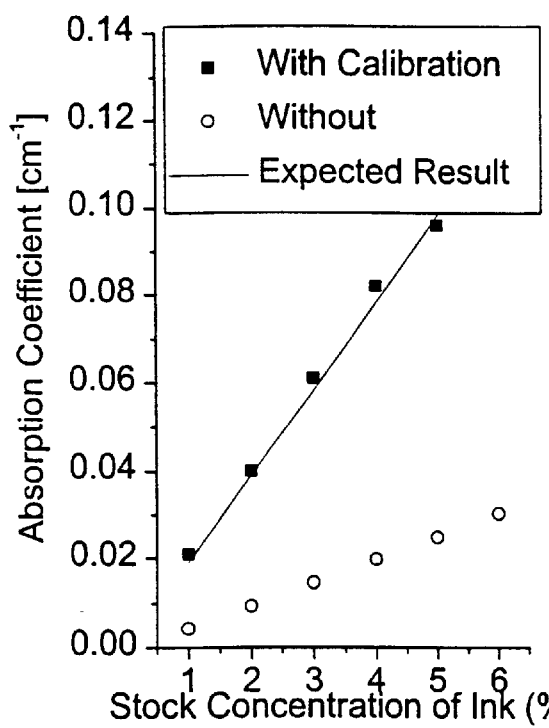
FIGS. 6a–6b are graphs of optical coefficients determined in Example 2 based on experimental data.

In a first experiment, the absorption coefficient was incrementally increased by adding more India ink. The Intralipid concentration, and hence the reduced scattering coefficient was kept constant. The calibration method, e.g., steps 300–330 of FIG. 3, was then used to determine the coupling constants, the absorption coefficient for the varying concentrations of India Ink, and the constant reduced scattering coefficient. FIG. 6a shows the plot of the absorption coefficient determined with the calibration method (filled squares) as a function of the ink concentration. The results were compared with absorption coefficients (open circles) determined without the calibration method, in which case the measured signals g(i,j) were fit directly to a homogeneous model for the bath.

Expected results based on independent spectrophotometer measurements are plotted as a straight line and show the improvement based on the calibration method. For example, at a concentration of 3% of ink solution, the spectrophotometer measurement was of $0.052$ $cm^{-1}$, compared to $0.06$ $cm^{-1}$ and $0.02$ $cm^{-1}$, with and without the calibration, respectively. The reduced scattering coefficients were determined to be $9.3$ $cm^{-1}$ and $24$ $cm^{-1}$ with and without the calibration, respectively. Once again the result with the calibration was much closer to an independent measurement, which was $10$ $cm^{-1}$ for the reduced scattering coefficient.

Figure 6B:
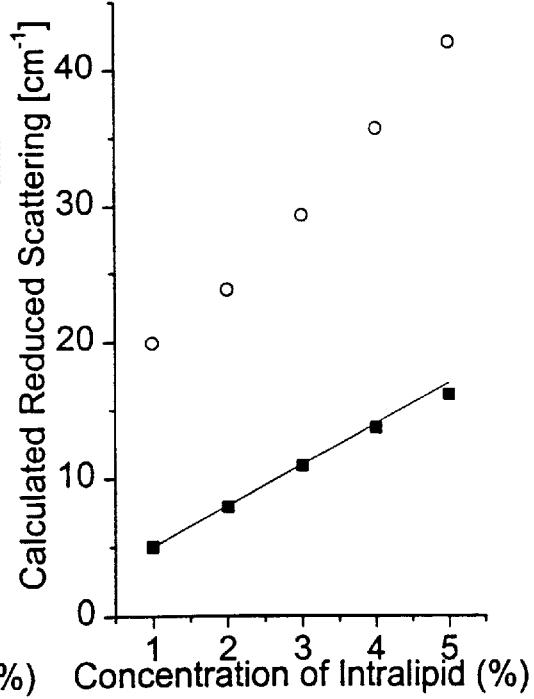

Improved accuracy because of the calibration was similarly observed in a second set of experiments in which the scattering coefficient was incrementally increased by adding more India ink. The results for the second set of experiments are shown in FIG. 6b.

3. Simulated Calibration Results

To determine how the variance in the calculated optical properties depends on the variance in the coupling coefficients, both with and without use of the calibration procedure, simulations were performed to mimic the conditions in Example 2. To generate the simulated measurements for the calibration, forward calculations were performed with the coupling coefficients of each source and detector randomly varied between 0.5 and 1. About 1% Gaussian noise was then added to the forward calculation.

The simulated data was then analyzed with and without the calibration method to determine the absorption coefficient and reduced scattering coefficient. The results for absorption and constant scattering are shown in the FIGS. 7a and 7b show the results for the absorption coefficient and the reduced scattering coefficient, respectively, as absorption is being increased, and FIGS. 7c and 7d show the corresponding results as scattering is being increased. The filled squares indicate results with the calibration, the open circles indicate results without the calibration, and the line indicates a fit to expected results. The error bars represent the standard deviation caused by varying the coupling coefficients in the simulations. The simulations show that the calibration method improves both the mean and standard deviation of the determined coefficients.

4. Simulated Results for a Hidden Object

Simulations were performed to apply the calibration method to enhance the accuracy of imaging by diffuse optical tomography of an object hidden in a highly scattering medium. The background medium was simulated to have a reduced scattering coefficient of $10$ $cm^{-1}$ and an absorption coefficient of $0.05$ $cm^{-1}$, and the object was a 2 mm by 2 mm by 2 mm cube centered at a depth of 1 cm under the optical probe array and having the same reduced scattering, but double the absorption, as those of the background medium. In lateral coordinates, the object was centered along the y-axis and +0.2 cm off-center along the x-axis. The positions of the 9 sources and 16 detectors were the same as that described in Example 2 (see FIG. 5). The coupling coefficient for each source and detector was randomly varied between 0.5 and 1 and about 1% Gaussian noise was added to the simulated measurements. The calibration method was then applied to the simulated measurements. The perturbation expansion of Equations (11) and (12) and the SIRT technique were used to perform the inverse calculation.

Figure 8A:
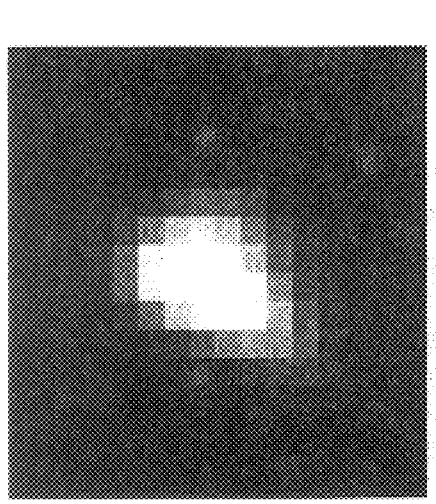
FIGS. 8a–8b are reconstructed DOT images determine with (FIG. 8b) and without (FIG. 8a) the calibration method described herein for the simulation of Example 4.
Figure 8B:
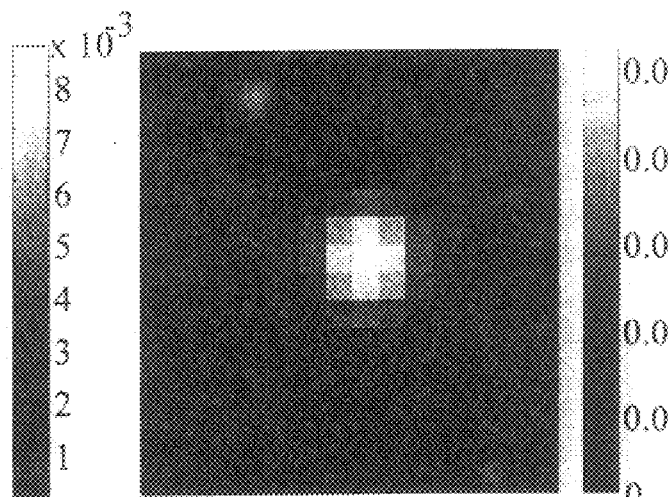
Figure 10A:
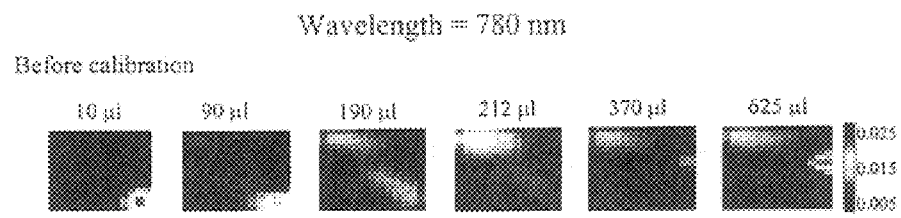
FIGS. 10a–10d are reconstructed DOT images of experimental data from Example 5.
Figure 10B:
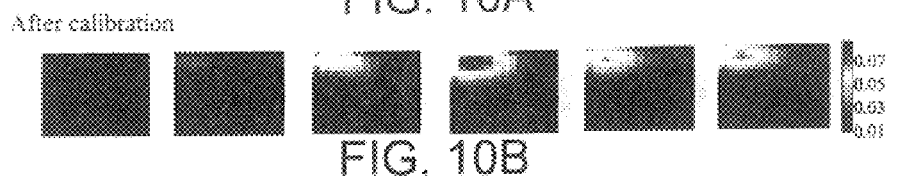
Figure 10C:
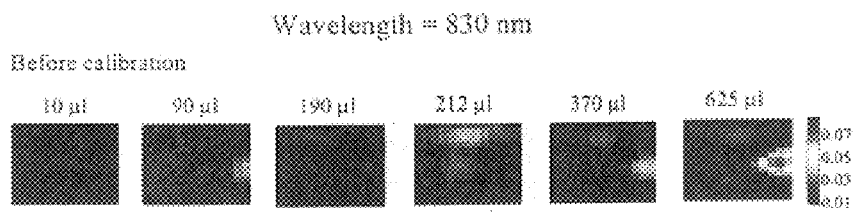
Figure 10D:
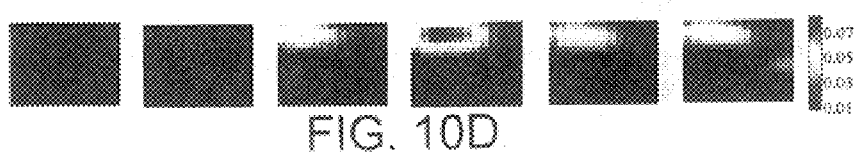

FIGS. 8b and 8a show a reconstructed image of the object with and without, respectively, application of the calibration method to correct the simulated measurement prior to the inverse calculation. FIGS. 8a and 8b correspond to one set of coupling coefficients and noise. The simulations were repeated with 100 different sets of randomly chosen coupling coefficients and noise to observe the variance in the reconstructed images. Application of the calibration method reduced the variance by more than 95% in these simulations.

5. Experimental Imaging of Hematomas in a Piglet Model

A piglet model was used in this study. The experimental set-up was a hybrid system of diffuse optical tomography and x-ray CT. Measurements were made on the bench of the x-ray scanner.

A one-week old piglet, weighted 3 kg, was sedated, incubated, and ventilated during the experiment. The femoral artery was catheterized for continuous blood pressure monitoring, fluid infusions, and blood extractions. The blood taken from the femoral artery was delivered through two small needles inserted 2 cm through scalp, skull, and brain tissue with a separation of about 2 cm. The combined thickness of the scalp and skull is about 1 cm, so the blood was injected into the brain at a depth of about 1 cm. The injection speed was controlled by a step motor at a rate of 42 $\mu$l/minute. Total 625 $\mu$l blood was injected for each bleed in 15 minutes respectively. Images were reconstructed every 15 seconds. Bleed A was created first, then bleed B. The optical probe was placed on top of the piglet's head.

Figure 9:
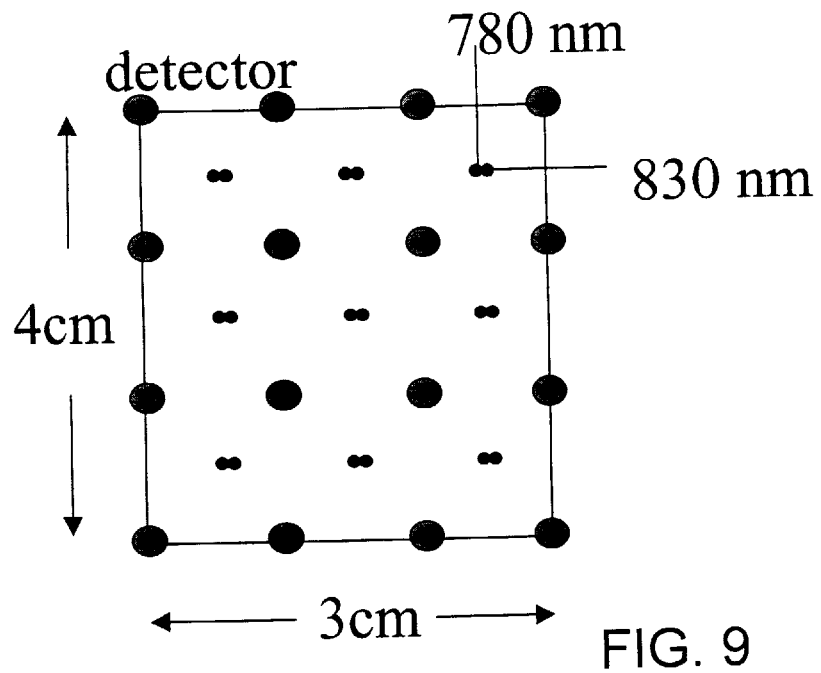
FIG. 9 is a schematic diagram of the optical arrangement of the sources and detectors of Example 5.

Referring to FIG. 9, the probe has 16 detectors (large circles) and 9 sources at each of 780 nm and 830 nm. The positions of bleeds A and B relative to the probe are also shown in FIG. 9. Before starting to inject the blood into A, a baseline was measured and used to find the coupling coefficient of each source-detector channel and also the background optical properties. The calculated absorption and effective scattering coefficients were $0.0672$ $cm^{-1}$ and $8.44$ $cm^{-1}$, respectively, at 780 nm, and $0.0666$ $cm^{-1}$ and $7.61$ $cm^{-1}$, respectively, at 830 nm. These values correspond to a $SO_2$ of 58% and HbT of 78 $\mu$l/mol. After bleed A was generated, another baseline was measured before injecting blood into B. X-ray CT images were taken after the optical measurements to identify the positions of the bleeds.

2D images were reconstructed based on the DOT measurements using simultaneous iterative reconstruction technique (SIRT) and assuming that the piglet head is semi-infinite. FIGS. 10a–d shows the time-course of the reconstructed images of bleed A at both wavelengths, both with and without using the calibration method to correct the DOT measurements. FIGS. 10a–d show that the application of the calibration method greatly reduces the presence of artifacts in the bottom and right sides of the images. The calibration method also improves the image amplitude.

Figure 11A:
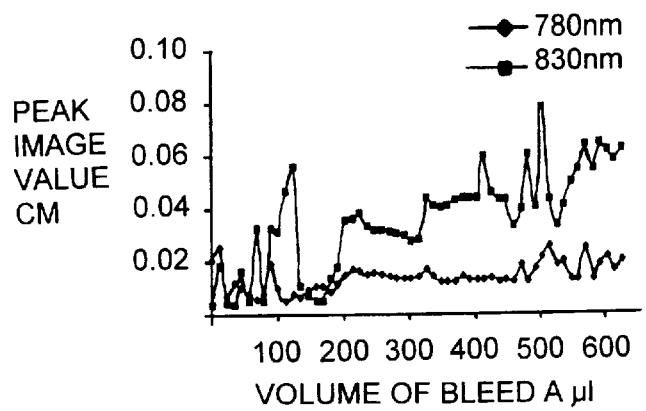
FIGS. 11a–b are graphs of peak image values derived from the images of FIGS. 10a–10d.
Figure 11B:
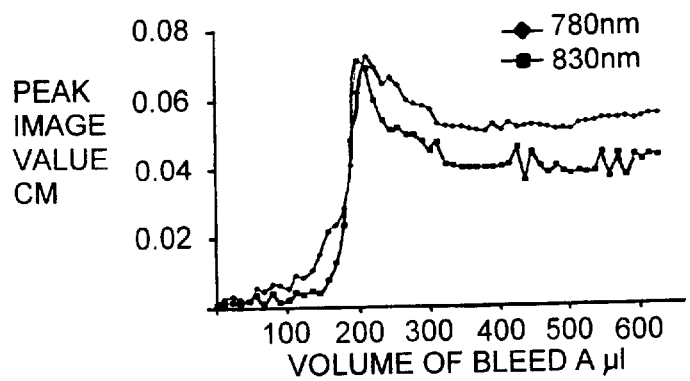

FIGS. 11a–b show a time-course plot of the peak image value of bleed A at the two wavelengths. Without calibration (FIG. 11a), the plot is noisy with no clear build up of the bleed. After the calibration (FIG. 11b), however, the development of the bleed is clearly visible.

Figure 12:
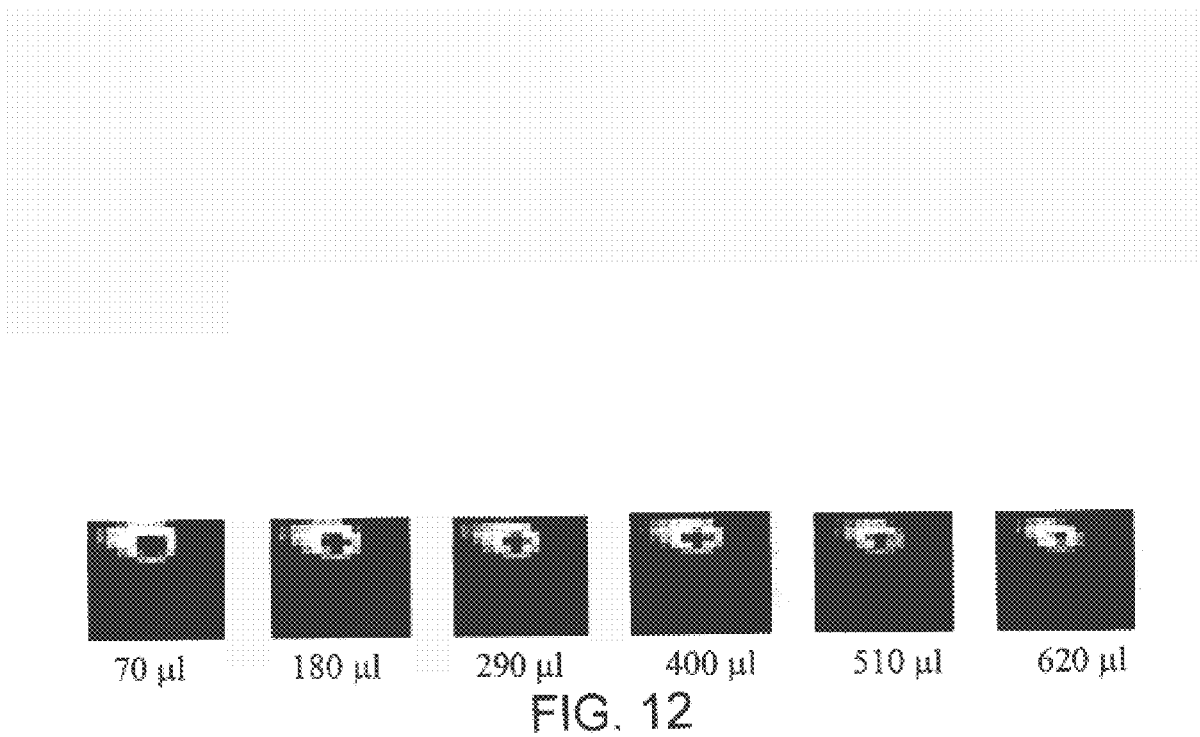
FIG. 12 is an additional reconstructed image of the experimental data from Example 5.

FIG. 12 shows time-course images of both bleeds A and B as the volume of bleed B was increased. The base line and coupling coefficient were the same as those used in reconstructing images of bleed A. The respective intensities of the A and B bleeds differ because their depths differ.

Other Embodiments

It is to be understood that while the invention has been described in conjunction with the detailed description thereof, that the foregoing description is intended to illustrate and not limit the scope of the invention, which is defined by the scope of the appended claims.

Other aspects, advantages, and modifications are within the scope of the following claims.

What is claimed is:

1. A system for making optical measurements of a sample, the system comprising:
   at least two optical sources which during operation couple optical radiation into the sample at spatially separated locations;
   at least two optical detectors positioned to receive optical radiation emitted from the sample at spatially separated locations in response to the optical radiation from the sources, wherein the signal $g(i,j)$ produced by the $j^{th}$ detector in response to the optical radiation from the $i^{th}$ source can be expressed as $g(i,j)=S^i D^j f(i,j)$, where $f(i,j)$ depends only on the properties of the sample, $S^i$ is a coupling coefficient for the $i^{th}$ source, and $D^j$ is a coupling coefficient for the $j^{th}$ detector; and
   an analyzer which during operation calculates the value of the product $S^l D^k$, wherein $S^l$ is a coupling coefficient for the $l^{th}$ source and $D^k$ is a coupling coefficient for the $k^{th}$ detector, for at least one of the source-detector pairs denoted by the superscripts l and k based on the signals produced by the detectors and simulated values of $f(i,j)$ corresponding to a model of the optical properties of the sample.

2. The system of claim 1, wherein during operation the analyzer calculates the value of the product $S^i D^j$ for every source-detector pair based on the detector signals and the simulated values of $f(i,j)$.

3. The system of claim 2, wherein the analyzer further calculates experimental values of $f(i,j)$ based on the calculated values of $S^i D^j$ and the signals $g(i,j)$ using the expression $g(i,j)=S^i D^j f(i,j)$, and performs an inverse calculation on the experimental values for $f(i,j)$ to determine spatial variations in at least one optical property of the sample.

4. The system of claim 3, wherein the at least one optical property comprises at least one of an absorption coefficient and a reduced scattering coefficient.

5. The system of claim 3, wherein during operation the analyzer modifies the model of the sample based on the determined spatial variations and repeats the calculation of the values of the product $S^i D^j$ for every source-detector pair using the modified model.

6. The system of claim 1, wherein the model corresponds to the sample being homogeneous.

7. The system of claim 1, wherein the analyzer simulates the values of $f(i,j)$ according to the expression:

$$f(i,j) \propto \frac{3\mu'_s}{4\pi |r_{ij}|} \exp\left[-(3\mu'_s \mu_a)^{\frac{1}{2}} |r_{ij}|\right]$$

where $|r_{ij}|$ is the distance between the $i^{th}$ source and the $j^{th}$ detector, where $\mu'_s$ is the reduced scattering coefficient, and where $\mu_a$ is the absorption coefficient.

8. The system of claim 1, wherein the analyzer calculates the value of the product $S^l D^k$ by minimizing the expression:

$$F(S^l D^k) = \sum_{i=1}^{N_s} \sum_{j=1}^{N_d} \left(\frac{L(i,j,k,l)}{S^l D^k} f(i,j) - g(i,j)\right)^2,$$

where $$L(i,j,k,l) = A_s^{ik} A_d^{jl}$$

$$A_s^{ik} = \frac{N_s}{N_d} \sum_{j=1}^{N_d} \frac{g(i,j)}{f(i,j) \cdot \sum_{ii=1}^{N_s} \frac{g(ii,j)}{f(ii,j)} \cdot \frac{f(ii,k)}{g(ii,k)}}$$

$$A_d^{jl} = \frac{N_d}{N_s} \sum_{i=1}^{N_s} \frac{g(i,j)}{f(i,j) \cdot \sum_{jj=1}^{N_d} \frac{g(i,jj)}{f(i,jj)} \cdot \frac{f(l,jj)}{g(l,jj)}}$$

and $N_S$ is the number of sources and $N_D$ is the number of detectors.

9. The system of claim 8, wherein the model corresponds to the sample being homogeneous, and wherein during operation the analyzer calculates at least one of the absorption coefficient $\mu_a$ and the reduced scattering coefficient $\mu'_s$ by minimizing $F(S^l D^k)$ with respect to the product $S^l D^k$ and the at least one of the absorption and scattering coefficients, $F(S^l D^k)$ implicitly depending on $\mu_a$ and $\mu'_s$ through $f(i,j)$.

10. The system of claim 9, wherein during operation the analyzer calculates both of the absorption and scattering coefficients by minimizing $F(S^l D^k)$ with respect to the product $S^l D^k$ and the absorption and scattering coefficients.

11. The system of claim 8, wherein the analyzer calculates the product $S^m D^n$ for every source-detector pair by minimizing $F(S^m D^n)$.

12. The system of claim 8, where the analyzer calculates the product $S^i D^j$ for every remaining source-detector pair according to $$S^i D^j = \frac{L(i,j,k,l)}{S^l D^k}.$$

13. The system of claim 1, wherein $g(i,j)$, $f(i,j)$, $S^i$, and $D^j$ are all real-valued.

14. The system of claim 1, wherein the sources couple continuous-wave optical radiation into the sample.

15. A method for calibrating an optical measurement system including at least two optical sources and at least two optical detectors, wherein the sources couple optical radiation into a sample at spatially separated locations and the detectors are positioned to receive optical radiation emitted from the sample at spatially separated locations and generate signals in response to the optical radiation from the sources, the method comprising:

provided the signals generated by the detectors, wherein the signal g(i,j) generated by the $j^{th}$ detector in response to the optical radiation from the $i^{th}$ source can be expressed as g(i,j)=$S^i D^j$f(i,j), where f(i,j) depends only on the properties of the sample, $S^i$ is a coupling coefficient for the $i^{th}$ source, and $D^j$ is a coupling coefficient for the $j^{th}$ detector; and calculating the value of the product $S^l D^k$ for at least one of the source-detector pairs based on the signals generated by the detectors and simulated values of f(i,j) corresponding to a model of the optical properties of the sample.

16. A computer readable medium comprising a program which causes a processor to perform the steps of claim 15.

17. The method of claim 15, wherein the value of the product $S^l D^k$ is calculated for the product $S^i D^j$ for every source-detector pair based on the detector signals and the simulated values of f(i,j).

18. The method of claim 17, further comprising calculating experimental values of f(i,j) based on the calculated values of $S^i D^j$ and the signals g(i,j) using the expression g(i,j)=$S^i D^j$f(i,j), and performing an inverse calculation on the experimental values for f(i,j) to determine spatial variations in at least one optical property of the sample.

19. The method of claim 15, wherein values of f(i,j) are simulated according to the expression:

$$f(i,j) \propto \frac{3\mu'_s}{4\pi|r_{ij}|} \exp\left[-(3\mu'_s\mu_a)^{\frac{1}{2}}|r_{ij}|\right]$$

where $|r_{ij}|$ is the distance between the $i^{th}$ source and the $j^{th}$ detector, where $\mu'_s$ is the reduced scattering coefficient, and where $\mu_a$ is the absorption coefficient.

* * * * *

UNITED STATES PATENT AND TRADEMARK OFFICE
CERTIFICATE OF CORRECTION

PATENT NO. : 6,549,284 B1  Page 1 of 1
DATED : April 15, 2003
INVENTOR(S) : David Alan Boas and Xuefeng Cheng It is certified that error appears in the above-identified patent and that said Letters Patent is hereby corrected as shown below:

<u>Title page,</u>
Item [60], replace "2000" with -- 1999 --

<u>Column 1,</u>
Line 9, replace "2000" with -- 1999 --

<u>Column 2,</u>
Line 24, replace "land" with -- and --

<u>Column 4,</u>
Line 2, replace "lo" with -- to --
Line 11, replace "calculates" with -- calculate --
Line 27, replace "includes" with -- include --

<u>Column 5,</u>
Line 45, replace "calculates" with -- calculate --

<u>Column 11,</u>
Line 54, after "$r_d$" insert -- , --

<u>Column 13,</u>
Line 37, insert -- , -- between "objective" and "the"

Signed and Sealed this

Sixteenth Day of December, 2003

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,549,284 B1 |
| APPLICATION NO. | : 09/662862 |
| DATED | : April 15, 2003 |
| INVENTOR(S) | : David Alan Boas and Xuefeng Cheng |

It is certified that error appears in the above-identified patent and that said Letters Patent is hereby corrected as shown below:

<u>Column 1</u>
Line 11, insert the following: --This invention was made with Government support under Grant No. NS038842 awarded by the National Institutes of Health and Grant No. DAMD17-99-2-9001 awarded by the U.S. Department of the Army. The Government has certain rights to this invention.--

Signed and Sealed this

Twenty-first Day of July, 2009

JOHN DOLL
*Acting Director of the United States Patent and Trademark Office*